United States Patent [19]

Kira

[11] Patent Number: 4,623,347

[45] Date of Patent: * Nov. 18, 1986

[54] ANTITHROMBOGENIC ELASTOMER PRODUCTS

[75] Inventor: Kazuaki Kira, Kobe, Japan

[73] Assignee: Kanegafuchi Kagaku Kogyo Kabushiki Kaisha, Osaka, Japan

[*] Notice: The portion of the term of this patent subsequent to Jul. 9, 2002 has been disclaimed.

[21] Appl. No.: 721,018

[22] Filed: Apr. 8, 1985

Related U.S. Application Data

[60] Division of Ser. No. 606,559, May 7, 1984, Pat. No. 4,528,343, which is a continuation of Ser. No. 384,210, Jun. 2, 1982, abandoned.

[30] Foreign Application Priority Data

Jun. 22, 1981 [JP] Japan .................................. 56-97270
Apr. 27, 1982 [JP] Japan .................................. 57-72298

[51] Int. Cl.$^4$ ............................................... A61F 2/06
[52] U.S. Cl. .................................... 623/1; 128/334 R; 604/403; 623/11; 623/66
[58] Field of Search ..................... 3/1.4; 525/440, 453, 525/460; 604/403; 623/1, 11, 66; 128/334 R

[56] References Cited

U.S. PATENT DOCUMENTS

| | | | |
|---|---|---|---|
| 3,246,048 | 4/1966 | Haluska | 260/824 |
| 3,567,499 | 3/1971 | Klebert | 117/139.5 |
| 4,528,343 | 7/1985 | Kira | 528/26 |

FOREIGN PATENT DOCUMENTS 2073219 10/1981 United Kingdom .

Primary Examiner—Wilbert J. Briggs, Sr.
Attorney, Agent, or Firm—Armstrong, Nikaido, Marmelstein & Kubovcik

[57] ABSTRACT

Antithrombogenic elastomers comprising polyurethane or polyurethane urea, containing an organic silicone polymer in the main chain. A process for manufacturing such elastomers and molded products of such elastomers, are also disclosed.

8 Claims, No Drawings

ANTITHROMBOGENIC ELASTOMER PRODUCTS

This is a division of application Ser. No. 606,559 filed May 7, 1984, now U.S. Pat. No. 4,528,343, which is a continuation of application Ser. No. 384,210 filed June 2, 1982 now abandoned.

BACKGROUND OF THE INVENTION

1. Field of the Invention

This invention relates to antithrombogenic elastomers, molded products made thereof, and a process for producing such elastomers.

2. Description of the Prior Art

Antithrombogenic elastomers exhibit their salient features when they are used at a site whereat they are brought into contact with blood. They are required for the manufacture of medical instruments which are brought into direct contact with blood, particularly artificial hearts, and other artificial organs. They are used for making, for example, blood vessel catheters, monitoring tubes, blood bags, externalcorporeal circulation circuits, such as artificial kidneys and mechanical hearts and lungs, A-V shunts, blood bypass tubes, artificial hearts, auxiliary artificial hearts, blood pumps, balloon pumps, etc. These applications essentially require the use of elastomers which are superior in antithrombogenic properties, mechanical properties (such as, for example, mechanical strength, elasticity and durability) and moldability.

Specific examples of antithrombogenic elastomers which are known in the art, include general purpose high molecular materials, such as soft vinyl chloride, polyurethane and silicone rubber; segmented polyurethane, such as Biomer of Ethicon, U.S.A.; heparinized polyurethane elastomer, which is disclosed in Japanese Pat. No. 13729/80; and a copolymer of polysiloxane and polyurethane bonded directly to each other by nitrogen and silicon, which is disclosed in U.S. Pat. No. 3,562,352.

None of these prior art compositions are entirely satisfactory for the use desired. For example, the general purpose high molecular materials are somewhat deficient in antithrombogenic properties. The segmented polyurethane is inferior in antithrombogenic properties, although it has high degree of mechanical strength. The heparinized polyurethane elastomer is very low in antithrombogenic properties after it has released heparin. Also, since heparin is physiologically active, this elastomer involves complex problems in molding and sterilization, and is thus costly to use. The copolymer disclosed in U.S. Pat. No. 3,562,352 (which is known under the tradename AVCOTHANE) is superior to any other known material in antithrombogenic properties, and is thus often used clinically. However, this copolymer is inferior in mechanical properties, when compared, for example, to segmented polyurethane. Moreover, its antithrombogenic properties, depend largely on the molding conditions, and are not always satisfactory. The copolymer is manufactured by a process which comprises mixing solutions of polyurethane and polysiloxane having reactive terminal groups, and reacting them when a molded product is formed therefrom. The reaction is shown by the following reaction equation:

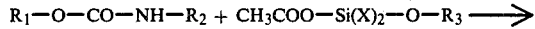
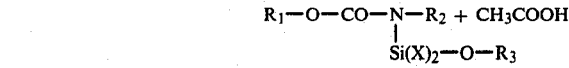

wherein $R_1$ and $R_2$ each stand for a polyurethane chain segment, $R_3$ stands for a polysiloxane chain, and X stands for a substituent bonded to a silicon atom. As is obvious from this equation, it is in substance a graft copolymer. Also, since polysiloxane has at least two reactive terminal groups, it is a thermosetting resin containing polysiloxane as a cross linking agent. This resin is therefore, moldable by only a limited number of methods, such as by coating and dipping. This limitation to the molding method necessitates storage of the resin in the form of a solution. Disadvantageously, if the polyfunctional terminal groups of polyurethane and polysiloxane react with each other during storage, the solution will become highly viscous or gelatinous, and would be unusable.

Thus, there is in the art a large deficiency. To now, there does not exist any antithrombogenic elastomer which has the combined properties of excellent antithrombogenic properties, excellent mechanical properties, and molding properties which enable a wide range of molding methods.

SUMMARY OF THE INVENTION

It is, therefore, an object of the invention to provide an antithrombogenic elastomer which is superior and reliable in antithrombogenic properties, is excellent in mechanical properties, and is moldable by a wide range of different molding methods.

As a result of extensive research, the inventors hereof have discovered that polyurethane or polyurethane urea, containing an organic silicone polymer in the main chain, is superior and reliable in antithrombogenic properties, and excellent in mechanical properties, and is moldable by a wide variety of different molding methods.

Another object is to provide molded products of such antithrombogenic elastomers.

A further object is to provide a method for producing such elastomers.

DETAILED DESCRIPTION OF THE INVENTION

This invention provides an antithrombogenic elastomer comprising polyurethane or polyurethane urea, containing an organic silicone polymer in this main chain. The preferred quantity of the silicone polymer in the elastomer of this invention, is in the range of from 1 to 50% by weight, preferably 3 to 20 weight percent, and more preferably 4 to 15 weight percent, in order to ensure its antithrombogenic properties. If the quantity of the organic silicone polymer exceeds 50% by weight, the antithrombogenic and mechanical properties are likely to drop.

The organic silicone polymer of this invention is an organic silicon containing polymer having a molecular weight of at least 200, preferably 500 to 10,000, and more preferably 700 to 3,000 (when the molecular weight was determined throughout herein, by the vapor pressure equilibrium method or by osmometry). Although there is no particular limit to the method of bonding organic silicon, it is preferable to employ polysiloxane in order to ensure the antithrombogenic properties of the elastomer. Methylphenylpolysiloxane, fluoroalkylmethylpolysiloxane and polydimethylsiloxane, can for example be employed. Polydimethylsiloxane is particularly preferred. The most preferable form in which polydimethylsiloxane may be incorporated is expressed by the formula:

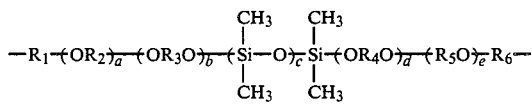

wherein $R_1$ to $R_6$ each stand for an alkylene group having one or more carbon atoms, a and e are each an integer of from 0 to 30, inclusive, b and d are each 0 or 1, and c is an integer of at least 2. $R_1$ to $R_6$ are each an alkylene group having one or more carbon atoms, and preferably an ethylene, propylene, butylene or hexamethylene group. The letters a and e each stand for an integer of from 0 to 30, inclusive, and preferably from 0 to 20, inclusive. The letters b and d may represent either 0 or 1, but if a long period of use in vivo is contemplated, it is preferable for each to represent 0, so that there will not be formed any Si—O—C bond that is easy to hydrolyze. The letter c represents an integer which depends on the molecular weight of polydimethylsiloxane which may be at least 200, preferably 500 to 10,000 and more preferably from 700 to 3,000.

The elastomer of this invention has a soft segment ratio of preferably 40 to 80% by weight, and more preferably 50 to 70 weight percent, in order to maintain satisfactory mechanical properties. The soft segment ratio is obtained in accordance with the following formula:

$$\frac{\text{Total molecular weight of soft segments}}{\text{Total molecular weight of elastomer}} \times 100 \, (\%)$$

An elastomer having a soft segment ratio which is lower than 40% by weight is likely to be deficient in elasticity, while an elastomer having a soft segment ration exceeding 80% by weight is likely to be inferior in mechanical strength, such as tensile strength.

The soft segments are segments between urethane or urea bonds, or between urethane and urea bonds, having a molecular weight of at least 500 (as measured by vapro pressure equilibrium method or by osmometry method) and a glass transition temperature not exceeding ordinary room temperature. Examples of the soft segments include polysiloxane, polyethers, polyesters, and their block copolymers. The preferred soft segments, apart from polysiloxanes, are polyethers, or polyesters, having a molecular weight of 500 to 6,000. It is more preferred to use polyethers having a high degree of hydrolysis stability in vivo and having a molecular weight of 700 to 3,000, particular

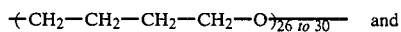 and

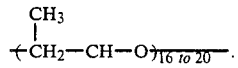

The elastomer of this invention is preferably an essentially thermoplastic elastomer composed of linear macromolecules which do not contain any cross linked structure.

The elastomer of this invention has an intrinsic viscosity ($\eta$) of preferably 0.2 to 2.0 dl/g, and more preferably 0.5 to 1.5 dl/g, as measured in dioxane at 32° C.

The elastomer of this invention imparts a substantially smooth surface to a molded product made thereof, and obtained under suitable molding conditions. The term "substantially smooth surface" as used herein means a surface of which examination by a scanning electron microscope of 1,000 magification does not reveal any physical uneveness with unevenness created by mold surface, foreign matter or other factors not directly associated with the nature of the elastomer per se, being disregarded. Suitable molding conditions mean dependence on any ordinarily conceivable means for formation of smooth surface, for example, the use of a full solution of the elastomer in a good solvent for molding by coating. When such suitable molding conditions are used, the inventive elastomer does not form any physically uneven surface, although it may form a microstructure of chemical phase separation as an ordinary block copolymer does. If a medical instrument is formed from a molded product of the inventive elastomer and obtained under the suitable conditions which form a substantially smooth surface, the instrument can be expected to be highly antithrombogenic.

The elastomer of the invention may be produced by a process which is further described hereinbelow. It is preferred to produce or manufacture the inventive elastomer by polymerizing essentially an isocyanate compound, a compound having an active hydrogen group and containing soft segments having a molecular weight of from 500 to 6,000, and a synthetic component having active hydrogen and/or isocyanate groups and containing in its main chain an organic silicone polymer, and, when desired, employing a chain extender, as discussed below. Temperatures, pressures, and other usual conditions utilized for producing thermoplastic polyurethane elastomers may be used as desired, provided the specific process steps and conditions of the invention are followed. The organic silicon content and soft segment ratio of the elastomer to be prepared may be first selected, and the quantity of the synthetic component then chosen to satisfy the foregoing. Then, the synthetic component may be added into a solvent, dissolved and reacted.

Although all of the synthetic component may be added together, it is preferable to react an isocyanate compound with a compound having active hydrogen groups and containing soft segments having a molecular weight of 500 to 6,000 first to form a prepolymer having isocyanate terminal groups, and react it with the synthetic component having active hydrogen groups and containing an organic silicone polymer in the main chain, followed by incorporation of a chain extender, if desired.

Alternatively, the prepolymer may be first reacted with a chain extender, and then, with the synthetic component having active hydrogen groups and containing an organic silicone polymer in the main chain.

It is advisable to add continuously and slowly, the synthetic component having active hydrogen groups and containing an organic silicone polymer in its main chain, and a highly reactive diamine chain extender. The reaction is performed under heating, or in the presence of a catalyst. Although it is possible to use any catalyst of the type often used for urethane synthesis, it is preferred to use triethyldiamine or other amines, diazabicycloundecene, or other catalyst which can be removed during molding, since the elastomer will be used for medical purposes.

Although it is possible to use any isocyanate compound of the type used for manufacture of polyurethane, diisocyanates are particularly preferred. Preferred examples of diisocyanate include tetramethylene diisocyanate, hexamethylene diisocyanate, cyclohexane-1,4-diisocyanate, 2,4-tolylene diisocyanate, 2,6-tolylene diisocyanate, a mixture of 2,4-tolylene diisoyanate and 2,6-tolylene diisocyanate, xylylene diisocyanate, 4, 4'-diphenylmethane diisocyanate, 1,4-phenylene diisocyanate, 1,3-phenylene diisocyanate, and naphthalene-1, 5-diisocyanate, and mixtures thereof. It is also possible to use any isocyanate compound obtained from regenerated compounds.

As regards the compound having active hydrogen groups and containing soft segments having a molecular weight of 500 to 6,000, it is possible to use any compound of the type used for reaction with isocyanate to form polyurethane, but is preferable to use a diol compound, such as polyethers, polyesters and polycaprolactones. It is more preferable to use a diol compound of the polyether series having a high degree of hydrolysis stability in vivo, and a molecular weight of 700 to 3,000, for example, polyethylene ether glycol, polypropylene ether glycol, polytetramethylene ether glycol, a polyethylene oxide-polypropylene oxide-polyethylene oxide copolymer, or a mixture thereof. Particularly preferred are those having the following formula:

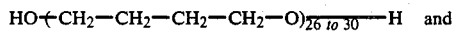

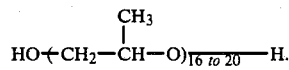

Preferred examples of diol compounds of the polyester series include polyesters obtained by polycondensation of ethylene glycol, propylene glycol, butylene glycol, diethylene glycol, pentamethylene glycol, cyclohexane-1,4-diol, cyclohexane-1, 4-dimethanol, or other glycols, or a mixture thereof, and adipic acid, maleic acid, succinic acid, phthalic acid, isophthalic acid, terephthalic acid, or other dibasic acids, or their derivatives such as acid esters or halides, and mixtures of such polyesters.

As regards the synthetic omponent containing an organic silicone polymer in its main chain, it is preferable to use a compound containing an organic silicone polymer in its main chain, and having two functional groups selected from active hydrogen and isocyanate groups. The preferred examples of such organic silicone polymer include polydimethylsiloxane, methylphenylpolysiloxane and fluoroalkylmethylpolysiloxane. The preferred functional group is an active hydrogen group, and preferred examples of groups having active hydrogen include carbinol, amino and mercapto groups, or a mixture thereof. A particularly preferred synthetic component containing an organic silicone polymer in the main chain is represented by the following formula:

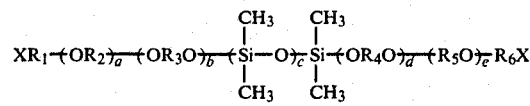

wherein $R_1$ to $R_6$ each stand for an alkylene group having at least one carbon atom, X stands for a group containing active hydrogen, a and e each stand for an integer of 0 to 30, inclusive, b and d are each 0 or 1, and c stands for 2 or a larger integer. More preferably, $R_1$ to $R_6$ are each an ethylene, propylene, butylene or hexamethylene group, X is a hydroxyl or amino group, a and e are both integers of 0 to 20, inclusive, and d and b are both zero, since the elastomer should preferably not containing any easily hydrolyzable Si—O—C bond for a long period of use in vivo. The integer for c depends of the molecular weight of polydimethylsiloxane, which is preferably at least 200, more preferably 500 to 10,000, and most preferably 700 to 3,000.

If any chain extender is used, it is preferable to use a chain extender having two active hydrogen groups, for example, aliphatic diamines, such as ethylenediamine, propylenediamine, butylenediamine and hexamethylenediamine; alicyclic and aliaromatic acid diamines, such as cyclohexanediamine, piperazine and zylenediamine; aromatic diamines, such as, tolylenediamine, phenyldiamine, and 4,4'-diphenylmethanediamine; hydrazines; glycols,such as ethylene glycol and 1,4-butanediol; or water.

Suitable examples of a solvent which may be used, includes N,N-dimethylformamide, N,N-dimethylacetamide, dimethylsulfoxide, N-methylpyrrolidone, dioxane and tetrahydrofuran. In order to fully dissolve the synthetic component and the resulting polymer,it is preferable to use a mixture of a low polar solvent, such as dioxane or tetrahydrofuran, and a high polar solvent, such as N,N-dimethylacetamide or N,N-dimethylformamide.

The elastomer synthesized as hereinbefore described may be used in either the form of a synthetic solution, or in the form of pellets which are obtained by precipitating the elastomer in water or the like, washing the precipitates carefully with water, ethanol or the like to remove impurities, and then drying.

The elastomer of this invention was tested for antithrombogenic properties in vitro, in accordance with the Lee White method (Izumi Kanai and Masamitsu Kanai, "Outline or Clinical Inspections", VI-81, Kinbara Publishing Co, 1970). The inventive elastomer showed a marked and surprising improvement over a segmented polyurethane elastomer (such as those used in the prior art) in total blood coagulation time, and was found to be superior in antithrombogenic properties. Samples molded under varying conditions were tested, and all were found to be highly reliable in antithrombogenic properties.

The elastomer of this invention was also found to be excellent in mechanical properties. It is generally believed that an antithrombogenic elastomer is required to have a tensile strength of at least 100 Kg/cm$^2$, and an elongation of at least 300 to 500%. The inventive elastomer showed a tensile strength of 100 to 500 kg/cm$^2$ and an elongation of at least 500%.

The inventive elastomer in the form of a solution lends itself well to molding by coating, dipping or casting. Pellets of the inventive elastomer are moldable by any ordinary molding method for a thermoplastic synthetic resin, such as for example, extrusion, injection molding, or press molding. Whether in the form of dry pellets or solution, the inventive elastomer showed a high degree of storage stability, was easy to handle, and showed a high degree of reproducibility. It was, in fact, an excellent antithrombogenic elastomer, which showed all the characteristics desired for use in medical applications.

The test results confirmed the usefulness of the inventive elastomer, for forming exposed surfaces of medical devices and instruments, which are brought into direct contact with blood. More specifically, it is useful for making, for example, artificial hearts, pumping chambers, auxiliary circulation devices, such as external corporeal circuits for auxiliary circulation devices, such as artificial kidneys and mechanical hearts and lungs, blood bags, balloon pumps and catheters, and the like.

The invention will now be further illustrated with examples which are not to be construed in any limiting sense.

EXAMPLE 1

A container, which had been fully dried and purged with nitrogen, was charged with 54.7 parts by weight of polytetramethylene ether glycol having a molecular weight of 2,000. It was dehydrated at a temperature of 90° C. and at a reduced pressure not higher than 0.1 mm Hg for a period of 30 minutes. After the glycol temperature had been adjusted to 50° C., 250 parts by weight of a mixed solvent consisting of dehydrated and purified dioxane and N,N-dimethylacetamide having a ratio by weight of 7:3 were added. Then, 27.35 parts by weight of 4,4'-diphenylmethane diisocyanate were added and dissolved under stirring. Diazabicycloundecene in the quantity of 0.05% by weight relative to the 4,4'-diphenylmethane diisocyanate, was added, as a catalyst, and stirring was continued for 30 minutes. Then, 4.75 parts by weight of ethylene glycol were added, and reaction was caused to take place for 30 minutes. The reaction was continued by dropping slowly a solution of 13.2 parts by weight of terminal carbinolpolydimethylsiloxane dissolved in 150 parts by weight of a mixed solvent consisting of dehydrated and purified dioxane and N,N-dimethylacetamide having a ratio by weight of 7:3. The terminal carbinol polydimethylsiloxane was of the formula:

$$HO-(CH_2CH_2O)_a-(Si(CH_3)_2-O)_b-(CH_2CH_2O)_c-H$$

wherein the sum of a and c had an average of 30.2 and b had an average of 14.2, and had a molecular weight of about 2,400. The polymer solution thus obtained, was placed in a large quantity of water, whereby the polymer was precipitated out. After the polymer had been washed carefully with water, it was dried, and washed with ethanol, by a Soxhlet extractor, whereby an antithrombogenic elastomer according to this invention was obtained.

The elastomer showed an intrinsic viscosity $\eta$ of 0.86 dl/g as measured in dioxane at 32° C. The elastomer was dissolved in a mixed solvent consisting of dioxane and N,N-dimethylacetamide having a ratio by weight of 7:3, and a cast film having a thickness of about 0.1 mm was formed from the elastomer solution. The mechanical properties of the cast film were determined by an apparatus called "Shimazu Autograph IS 2000". The film was found to have a smooth surface when it was examined by a scanning electron microscope of 1,000 to 5,000 magnification.

The antithrombogenic properties of the elastomer so obtained, were examined by a method which is hereinbelow described. The elastomer was dissolved in a mixed solvent consisting of dioxane and N,N-dimethylacetamide, having a ratio by weight of 7:3, to form an elastomer solution, having an elastomer content of about 5% by weight. This elastomer solution was coated on the inner surface of a test tube having an inside diameter of 10 mm and a length of 100 mm. About 1 ml of fresh blood which had just been collected, was placed in the test tube, and the time for coagulation of the blood was examined at a temperature of 37° C.

For comparison purposes, similar tests were conducted on segmented polyurethane (obtained in Comparative Example 1) and a test tube coated with a solution of same, as well as a test tube on which no coating whatsoever was applied. The solution was prepared by dissolving the segmented polyurethane in a mixed solvent consisting of dioxane and N,N-dimethylacetamide, having a ratio by weight of 7:3, and had a polymer content therein of 5% by weight.

The test results are shown in Table 1. The results confirm the superiority of the inventive elastomer in antithrombogenic and mechanical properties.

TABLE 1

| | Antithrombogenic | Mechanical Properties | |
|---|---|---|---|
| | Test-Blood Coagulation Time (min) | Tensile strength (kg/cm$^2$) | Elongation (%) |
| Example 1 | 68 to 72 | 350 | 670 |
| Comparative Example 1 | 30 to 38 | 400 | 550 |
| Uncoated Test tube (glass) | 10 to 13 | — | — |

A transparent, strong and elastic sheet having a thickness of 1 mm was prepared by press forming the elastomer of the invention at a temperature of 200° C. and at a pressure of 200 Kg/cm$^2$ for a period of 15 minutes. The antithrombogenic properties of this sheet were examined in the manner as described below. A 3 cm$^2$ elastomer sheet was placed on a watch glass having a cover and maintained at 37° C. A certain quantity of dog's ACD blood (i.e. noncoagulant, preservable blood prepared by adding sodium citrate, glucose, etc.) was placed on the sheet and the watch glass, and an aqueous solution of calcium chloride was added to the blood. The weights of coagulated blood (thrombus) were measured after certain periods of time. The ratio of thrombus formation was calculated by the following equation:

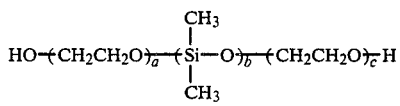

For comparison purposes, similar tests were conducted on similarly prepared sheets of segmented polyurethane elastomer obtained in accordance with Comparative Example 1, and of ordinary glass. The results are shown in Table 2. The results confirm the superiority in antithrombogenic properties of the sheet of the inventive elastomer over the prior art and over ordinary glass not having any elastomer coated thereon.

In the below Table 2, the sheet of inventive elastomer was examined by a scanning electron microscope of 1,000 to 5,000 magnifications, and found to have a smooth surface.

TABLE 2

| (Ratio of Thrombus Formation) | | | | | |
|---|---|---|---|---|---|
| | Duration of contact with Blood (min) | | | | |
| | 3 | 5 | 7 | 10 | 15 |
| Sheet of invention elastomer | 17.0% | 26.9% | 32.7% | 37.7% | 43.2% |
| Segmented polyurethane sheet | 25.4% | 44.7% | 55.2% | 65.5% | 77.2% |
| Glass | 61.5% | 85.2% | 96.9% | 99.5% | 99.5% |

COMPARATIVE EXAMPLE 1

A segmented polyurethane elastomer was prepared by repeating the procedure of Example 1, except that no terminal carbinolpolydimethylsiloxane was employed, and that the quantity of 4,4'-diphenylmethane diisocyanate was correspondingly reduced by 1.4 parts by weight.

EXAMPLE 2

A four-necked flask, which had been fully dried and purged with nitrogen, was charged with 52 parts by weight of polytetramethylene ether glycol having a molecular weight of 2,000. It was dehydrated at a temperature of 95° C. and a reduced pressure not higher than 0.1 mm Hg, for a period of 30 minutes. After the glycol temperature had been adjusted to 45° C., 200 parts by weight of a mixed solvent consisting of dehydrated and purified tetrahydrofuran and N,N-dimethylacetamide having a ratio by weight of 8:2 were added thereinto, and 14 parts by weight of 4,4'-diphenylmethane diisocyanate were added and dissolved. Diazabicycloundecene was added, as a catalyst, in a quantity of 0.03% by weight relative to 4,4'-diphenylmethane diisocyanate, and stirred for 30 minutes. Then, 18 weight parts 4,4'-diphenylmethane diisocyante, and 6 weight parts ethylene glycol were added, and reaction was performed for one hour. After the reaction temperature had been adjusted to ordinary room temperature (about 15° C.), the reaction was continued by adding continuously 10 parts by weight of double terminal 3-aminopropylpolydimethylsiloxane having a molecular weight of about 2,000, and dissolved in 200 parts by weight of a mixed solvent consisting of dehydrated and purified tetrahydrofuran and N,N-dimethylacetamide having a rato by weight of 8:2, whereby there was obtained a transparent, viscous synthetic solution. A large quantity of water was added into the solution for precipitation of a polymer. After the polymer had been carefully washed with water, and dried, it was washed with ethanol, by a Soxhlet extractor, to yield an antithrombogenic elastomer according to the invention. This elastomer was found to have an intrinsic viscosity $\eta$ of 0.75 dl/g in dioxane at 32° C. The antithrombogenic properties, tensile strength and elongation of the elastomer, were examined in accordance with the procedures of Example 1, except that a mixed solvent consisting of tetrahydrofuran and N,N-dimethylacetamide haing a ratio of 8:2 was used.

For comparison purposes, similar tests were conducted on segmented polyurethane obtained in accordance with Comparative Example 2, and a test tube coated with a solution of such polyurethane, as well as a test tube on which no coating whatsoever was applied.

The tests results are shown in Table 3. The results confirm the superiority of the elastomer obtained in our invention, in terms of both antithrombogenic properties, and mechanical properties.

COMPARATIVE EXAMPLE 2

A segmented polyurethane elastomer was prepared by repeating the procedure of Example 2, except that no double terminal 3-aminopropylpolydimethylsiloxane, was used, and that the quantity of 4, 4'-diphenylmethane diisocyanate (later added) was correspondingly reduced by 1.25 parts by weight.

TABLE 3

| | Antithrombogenic test-Blood coagulation time (min) | Mechanical Properties | |
|---|---|---|---|
| | | Tensile Strength (Kg/cm$^2$) | Elongation (%) |
| Example 2 | 50 to 60 | 430 | 630 |
| Comp. Ex. 2 | 30 to 38 | 450 | 550 |
| Glass | 9 to 12 | — | — |

EXAMPLE 3

Fifty eight parts by weight of dehydrated polypropylene ether glycol having a molecular weight of 1,000, 6.4 parts by weight of double terminal 3-hydroxypropylpolydimethylsiloxane having a molecular weight of about 1,000, and 32 parts by weight of 4, 4'-diphenylmethane diisocyanate were dissolved in 300 parts by weight of a mixed solvent consisting of dehydrated and purified tetrahydrofuran and N,N-dimethylacetamide having a ratio by weight of 8:2. Diazabicycloundecene, as a catalyst, was added into the solution in the quantity of 0.01% by weight relative to 4,4'-diphenyl methane diisocyanate, and reaction was performed at 60° C. for one hour, whereby a prepolymer having an isocyanate terminal group was obtained. After the reaction temperature had been lowered to ordinary room temperature (about 15° C.), 300 parts by weight of dehydrated and purified N,N-dimethylacetamide was added into the prepolymer solution to dilute it. The reaction was continued by adding slowly 300 parts by weight of a dehydrated and purified N,N-dimethylacetamide solution containing 3.6 parts by weight of ethylenediamine. The procedures of Example 1, were then repeated for the treatment of the polymer solution to produce purified elastomer. This elastomer was found to have an intrinsic viscosity $\eta$ of 0.56 dl/g in dioxane at 32° C. The antithrombogenic properties, tensile strength and elongation of the elastomer were examined in accordance with the procedures of Example 1, except that N,N-dimethylacetamide was employed. The elastomer coated on a glass test tube, was coagulated after the lapse of 50 to 65 minutes, while it showed a tensile strength of 470 Kg/cm$^2$ and a elongation of 600%.

The foregoing description is illustrative of the principles of the invention. Numerous modifications and extensions thereof would be apparent to the worker skilled in the art. All such modification and extensions are to be considered to be within the spirit and scope of the invention.

What is claimed is:

1. A method for the prevention of the clotting of blood in contact with medical devices comprising forming at least the blood contact surfaces of said devices from an elastomer comprising thermoplastic polyurethane or polyurethane urea containing 4 to 15 weight % of polysiloxane having a molecular weight of 500 to 10,000 in the main chain, and containing a polyether or a polyester having a molecular weight of 500 to 6,000 as a soft segment other than said polysiloxane.

2. The method of claim 1, wherein said polysiloxane has a molecular weight of 700 to 3,000.

3. The method of claim 1, wherein said elastomer has a soft segment content of from 40 to 80 weight %.

4. The method of claim 1, wherein said polysiloxane is a polydimethylsiloxane.

5. The method of claim 4, wherein said polydimethylsiloxane is of the formula:

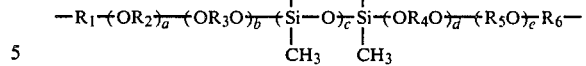

wherein $R_1$ to $R_6$ each stand for an alkylene group having at least one carbon atom, a and e are both integers of from 0 to 30, b and d are both 0 or 1, and c is an integer of from 6 to 134.

6. The method of claim 1, wherein said medical device is an artificial blood vessel.

7. The method of claim 1, wherein said medical device is a blood bypass tube.

8. In the manufacture of blood-contacting medical devices from materials of a non-mammalian origin, the improvement comprising forming at least the blood-contacting surface of said medical device from an elastomer comprising thermoplastic polyurethane or polyurethane urea containing 4 to 15 weight % of polysiloxane having a molecular weight of 500 to 10,000 in the main chain, and containing a polyether or a polyester having a molecular weight of 500 to 6,000 as a soft segment other than said polysiloxane.

* * * * *